United States Patent
Lampe et al.

(10) Patent No.: US 10,292,798 B2
(45) Date of Patent: May 21, 2019

(54) DEVICE AND METHOD FOR MOVING CARGO

(71) Applicants: Airbus Operations GmbH, Hamburg (DE); Airbus Operations SAS, Toulouse (FR); AIRBUS SAS, Blagnac (FR)

(72) Inventors: Dietrich Lampe, Dresden (DE); Kai Christensen, Bösel (DE); Claude Cuiller, d'Estretefonds (FR); Pierre-Eric Dereux, Colomiers (FR); Frank Feest, Toulouse (FR); Hyung-Jo Kim, Colomiers (FR); Knut Niemeck, Hamburg (DE); Kathryn Waidelich, Beauzelle (FR)

(73) Assignees: AIRBUS OPERATIONS GMBH, Hamburg (DE); AIRBUS OPERATIONS SAS, Toulouse (FR); AIRBUS SAS, Blagnac (FR)

( * ) Notice: Subject to any disclaimer, the term of this patent is extended or adjusted under 35 U.S.C. 154(b) by 290 days.

(21) Appl. No.: 15/185,474

(22) Filed: Jun. 17, 2016

(65) Prior Publication Data
US 2016/0368606 A1  Dec. 22, 2016

(30) Foreign Application Priority Data
Jun. 17, 2015  (EP) .................................... 15172591

(51) Int. Cl.
*B64D 9/00* (2006.01)
*A61C 13/15* (2006.01)
(Continued)

(52) U.S. Cl.
CPC .......... *A61C 19/003* (2013.01); *A61C 1/0015* (2013.01); *A61C 19/004* (2013.01);
(Continued)

(58) Field of Classification Search
CPC ... B64D 9/00; B64D 1/20; B64D 1/22; B64D 2009/006; A61C 19/004; B64C 1/20; B64C 1/22; B64C 1/30; B64C 1/34; B64F 1/32
See application file for complete search history.

(56) References Cited

U.S. PATENT DOCUMENTS

| | | |
|---|---|---|
| 3,756,544 A | 9/1973 | Bader |
| 3,869,028 A | 3/1975 | Sawada et al. |

(Continued)

FOREIGN PATENT DOCUMENTS

WO   2014049590 A1   4/2014

OTHER PUBLICATIONS

European Patent Office, Extended European Search Report for European Patent Application No. 15172591.8 dated Nov. 25, 2015.

*Primary Examiner* — Medhat Badawi
*Assistant Examiner* — Vicente Rodriguez
(74) *Attorney, Agent, or Firm* — Lorenz & Kopf LLP

(57) ABSTRACT

A device and method for moving cargo above a floor inside an aircraft comprises a rigid under-floor. The device comprises a body part for supporting the weight of the cargo, lifting means and for lowering the body part from its lifted position into a retracted position, and a drive unit for moving the body part. The method comprises the steps of providing at least two devices in an aircraft, positioning the devices beneath the cargo, wherein the body parts of the devices are in their retracted positions. The body parts are lifted such that the weight of the cargo is supported by the body parts and the cargo is lifted above the floor. The cargo is then moved to a desired position and lowered into their retracted positions such that the cargo is lowered and the devices are moved away vertically from the cargo.

5 Claims, 11 Drawing Sheets

(51) Int. Cl.
*B64C 1/20* (2006.01)
*B64C 1/22* (2006.01)
*A61C 1/00* (2006.01)

(52) U.S. Cl.
CPC .............. *B64C 1/20* (2013.01); *B64C 1/22* (2013.01); *B64D 9/00* (2013.01); *B64D 2009/006* (2013.01)

(56) References Cited

U.S. PATENT DOCUMENTS

| | | | | |
|---|---|---|---|---|
| 4,395,181 | A * | 7/1983 | Loomer | B65G 1/0414 254/4 B |
| 4,684,311 | A * | 8/1987 | Dickson-Wright | B65G 67/20 198/774.2 |
| 4,780,043 | A | 10/1988 | Fenner et al. | |
| 5,000,646 | A * | 3/1991 | Pietropaoli | B64D 9/00 244/137.1 |
| 5,374,151 | A * | 12/1994 | Matthews | B65G 67/20 414/343 |
| 9,387,931 | B2 * | 7/2016 | Himmelmann | B64D 9/00 |
| 2009/0304482 | A1 * | 12/2009 | Sanford | B64D 9/00 414/495 |
| 2015/0108276 | A1 * | 4/2015 | Panzram | B64D 9/00 244/137.1 |

* cited by examiner

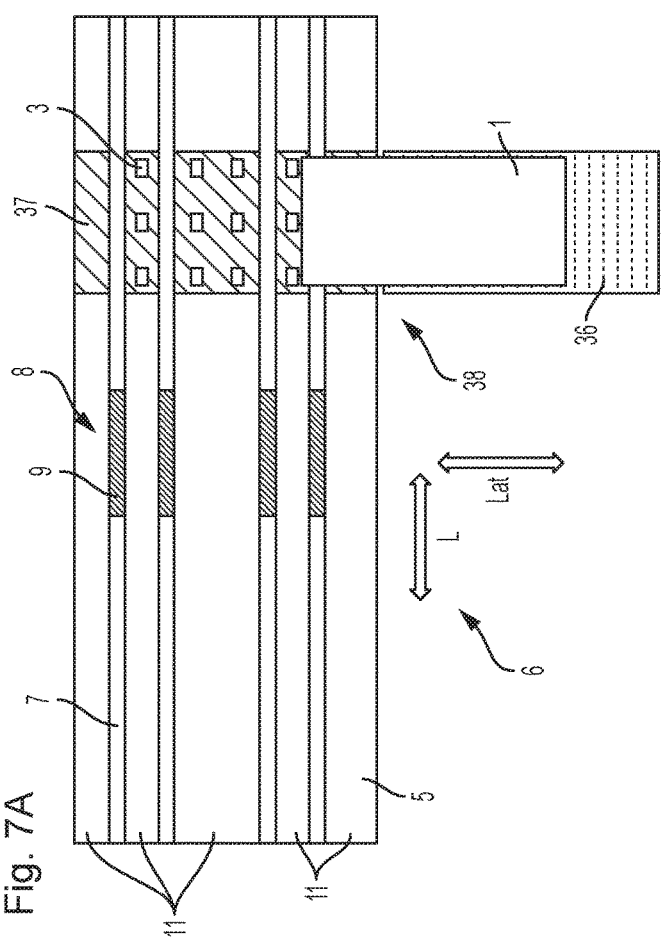
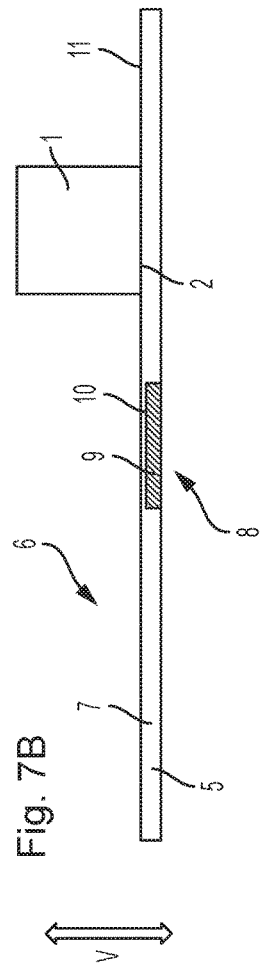
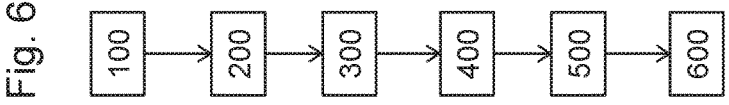

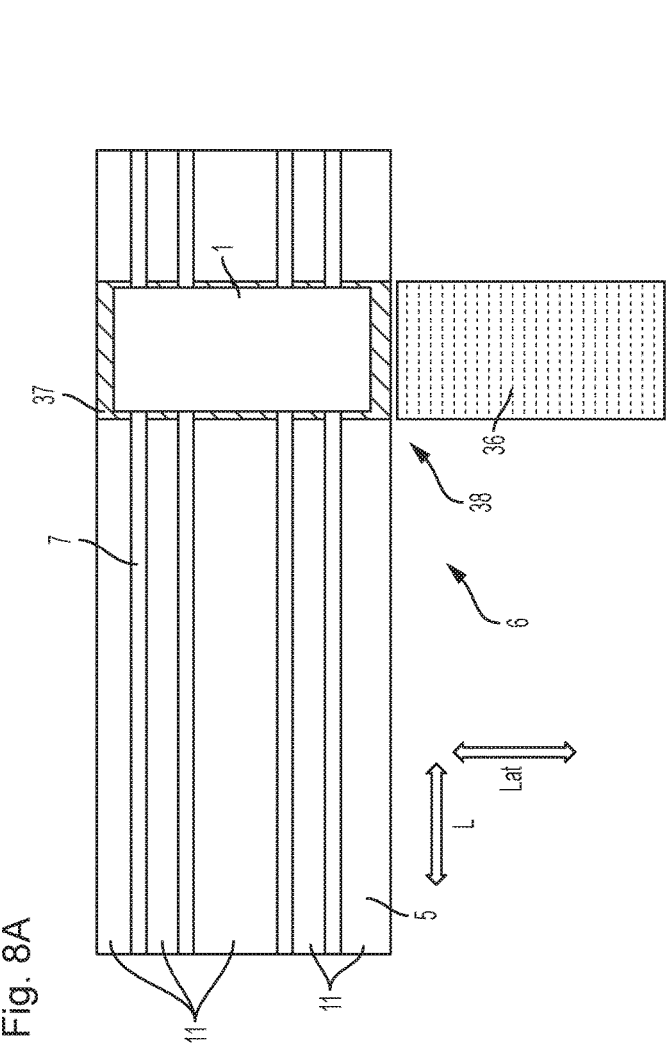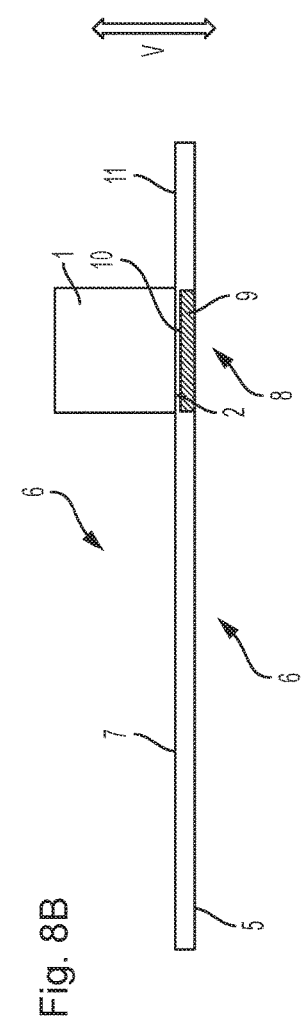
Fig. 8A
Fig. 8B

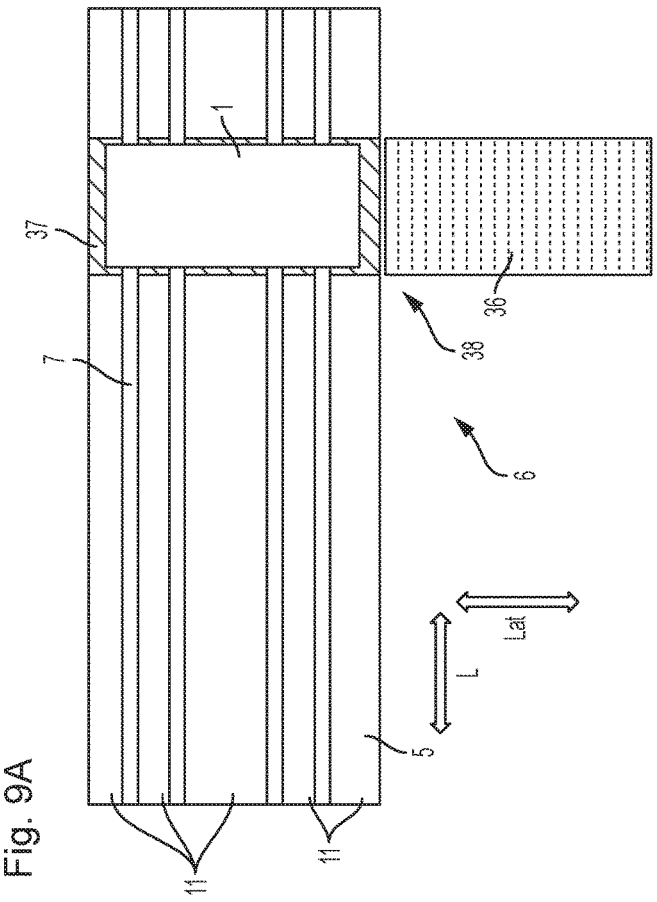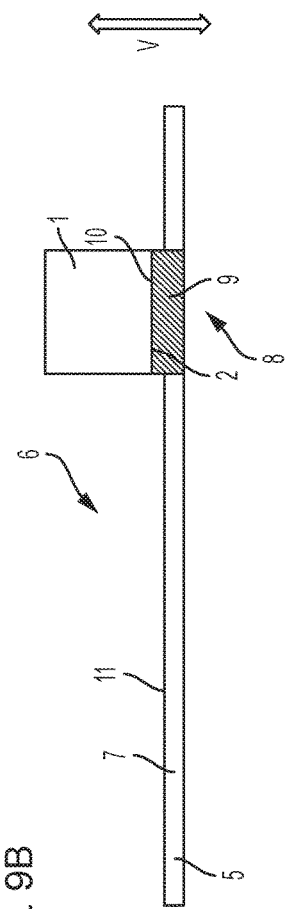

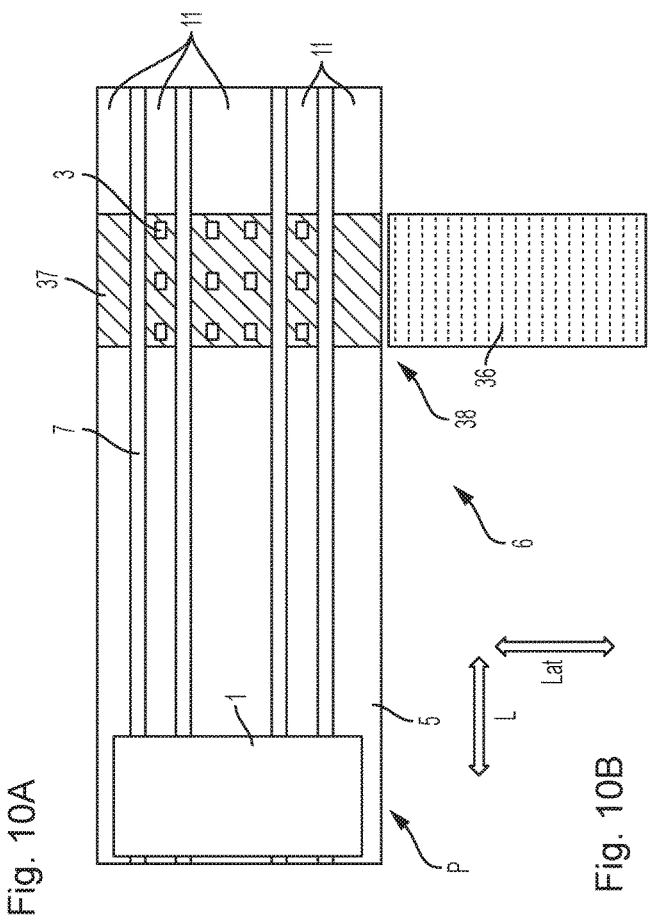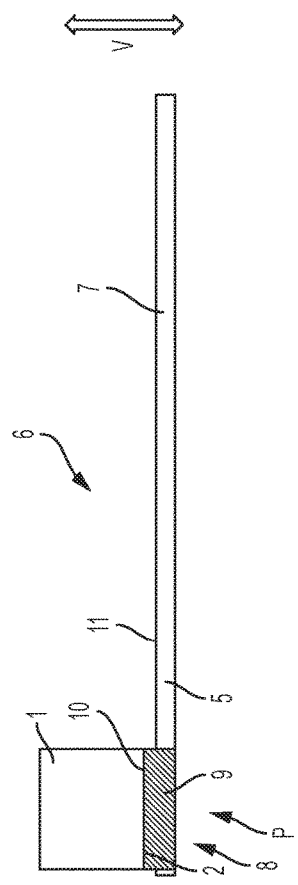

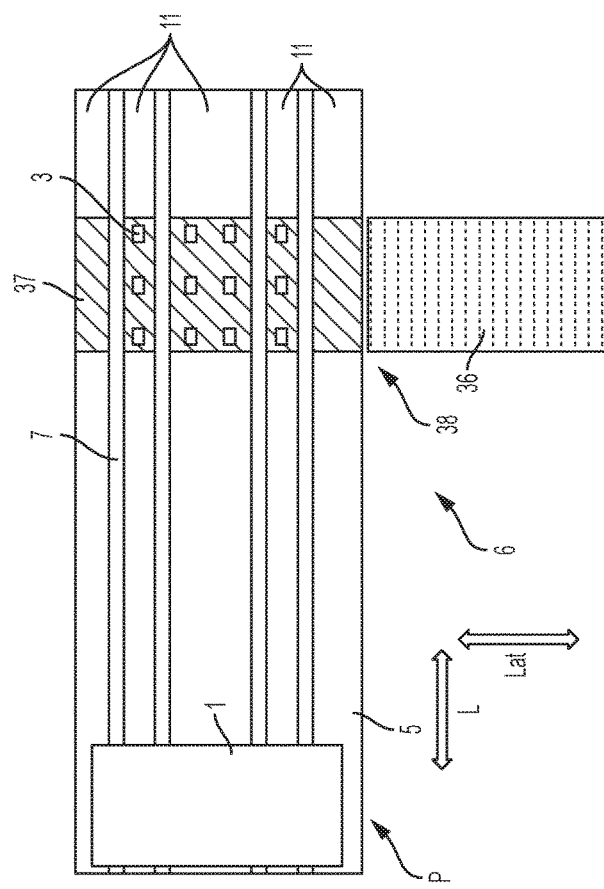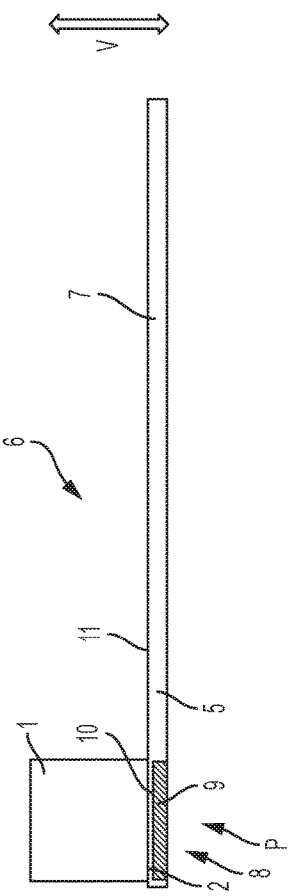

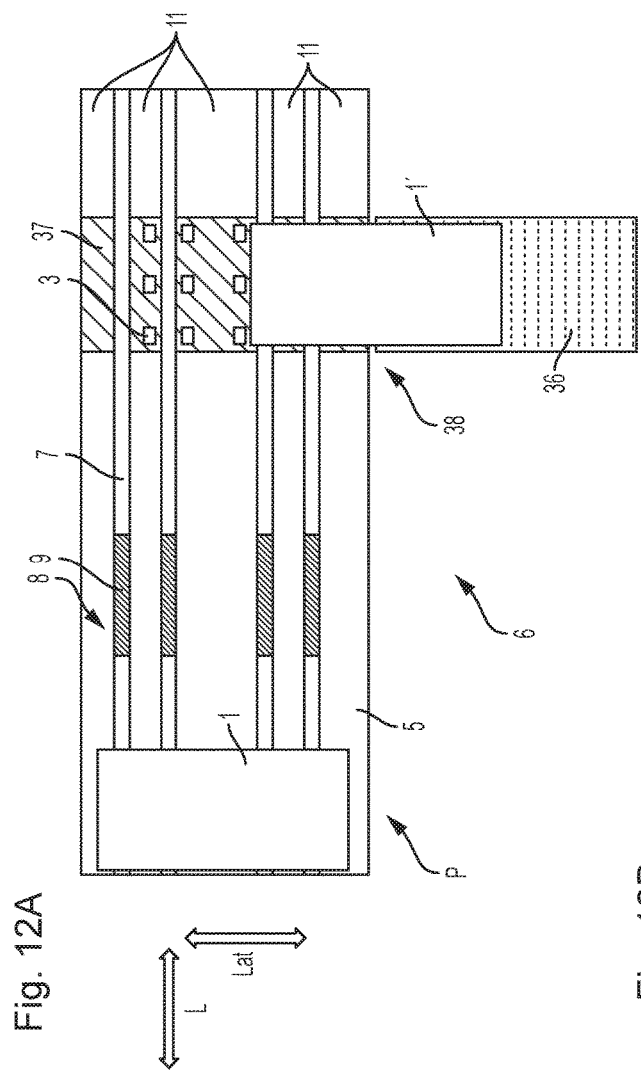
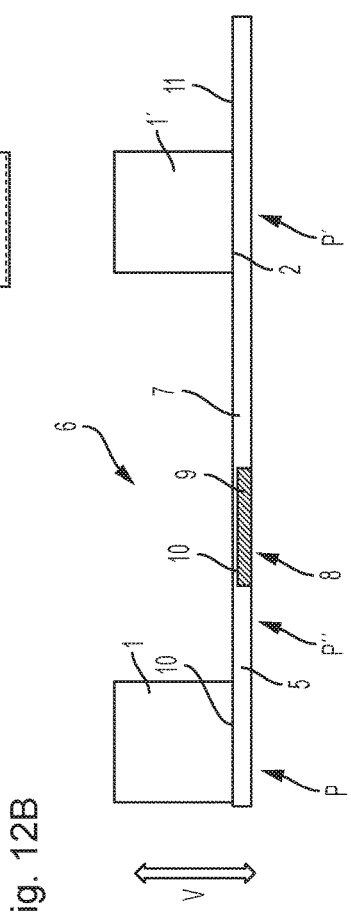
Fig. 12A
Fig. 12B

DEVICE AND METHOD FOR MOVING CARGO

CROSS-REFERENCE TO RELATED APPLICATION

This application claims priority to European Patent Application No. 15172591-8, filed Jun. 17, 2015, which is incorporated herein by reference in its entirety.

TECHNICAL FIELD

The embodiments described herein relate to a device and a method for moving cargo along a floor inside of an aircraft, especially cargo comprising a rigid under-floor such as cargo-containers or cargo pallets.

BACKGROUND

Other objects, desirable features and characteristics will become apparent from the subsequent summary and detailed description, and the appended claims, taken in conjunction with the accompanying drawings and this background.

Movement of containers and pallets into an aircraft may be provided by sideward transporting Roller Drives (typically called Power Drive Units—PDUs). Permanently installed ball mats may be used for an omnidirectional movement of containers and pallets within the entrance area of the aircraft. Movement within the cargo bays in longitudinal direction of the aircraft may be done by permanently installed PDUs with the containers and pallets being supported by free-wheeling rolls.

However, it has been shown that the weight of permanently installed rolls and PDUs may increase fuel consumption of the aircraft as well as costs for production, installation and maintenance.

SUMMARY

It may be an object of the embodiments described herein to provide an improved device and method which overcomes aforementioned disadvantages.

The embodiments described herein enable movement of cargo such as containers and other loads with rigid under-floor, wherein the device can be designed as a cargo-crawler, i.e. an aforementioned device having means for crawling, e.g. belts. The embodiments discard the need for aircraft cargo such as pallets or containers to stand on permanently installed rolls and to be moved by permanently installed PDUs. The devices can be used to lift containers and pallets a few centimeters, to move them to desired positions, and to let them down there again.

The device for moving cargo above a floor inside of an aircraft comprises a body part that is designed for supporting the weight of the cargo, lifting means that are arranged for lifting the body part into a lifted position and for lowering the body part from its lifted position into a retracted position, and a drive unit that is arranged for moving the body part.

The drive unit comprises means for moving the body part of the device, e.g. a motor and rollers, wheels or means for crawling that can be driven by the motor. In an example, the motor is an electric motor that can be powered by a battery or by a cable-power supply. Alternatively, the drive unit may comprise a rope for pulling the body part or a linear drive.

The lifting means are arranged for lifting the body part, e.g. a few centimeters, into its lifted position and to lower the body part again in order to bring it into its retracted position. For this purpose, the lifting means can e.g. comprise an electric motor or hydraulic/pneumatic elements that drive a lifting mechanism, wherein the electric motor or hydraulic/pneumatic elements are powerful enough not only to lift the body part but also to lift and support the weight of cargo such as a loaded pallet or a container.

In particular, the device is, in its retracted position, designed to be arranged beneath the cargo. In such a position, the body part can be lifted by the lifting means and be brought into its lifted position. During such a lifting, the body part can be brought into contact with the cargo such that the body part supports the weight of the cargo and lifts the cargo for a few centimeters such that the cargo can be lifted above a floor structure of an airplane. By moving the body part using its drive unit, the cargo can be moved above a floor inside of an aircraft. After moving the cargo to a desired position, the body part can be brought into its retracted position by lowering the body part by the lifting means. During such a lowering, the cargo is also lowered and the body part is vertically moved away from the cargo such that the weight of the cargo is supported from the floor structure of the airplane, and the device can be moved away from the cargo and moved to another cargo that shall be moved.

The device enables the reduction of the number of permanently installed rolls significantly, and PDUs are no longer needed. This can result in a reduction of weight, costs, and maintenance efforts. Further, the device can stay on an airport during flight of an aircraft and is not necessarily to be certified for aircraft use. This also saves costs. Also, cargo such as pallets or containers do not have to stand on rolls during a flight anymore that allows reducing the size, strength and weight of latches for the cargo and, thus, enables further weight and cost savings. Similarly, the pallets or containers do not stand on rolls, if the aircraft is on ground. This avoids a self-movement of the cargo due to gravity in the case of horizontally inclined cargo floors. As a result, security for personal is increased, there is no more need for breaking rolls, and it is not necessary to achieve a horizontal position of the cargo floor, if the aircraft is on ground, e.g. by an extra bow chassis. Furthermore, the device does not have to be permanently installed in an aircraft and can be exchanged easily that can reduce down time of the aircraft.

According to an embodiment, the drive unit is arranged for moving the body part in two perpendicular directions. For this purpose, the drive unit can comprise e.g. rollers or wheels with respective directions of rotation. Such perpendicular directions can e.g. be a longitudinal and a lateral direction of an aircraft.

According to a further embodiment, the body part comprises a cuboid shape and is dimensioned to fit in a U-shaped indentation of an aircraft floor structure. With such a design the device is enabled to move beneath a cargo that has to be moved in a very easy manner as existing indentations respectively profiles of a floor structure can be reused and changes to the aircraft structure are not necessary. Further, the cuboid shape enables an advantageous pressure distribution if the weight of a cargo is supported.

The body part may comprise a cover part that can be lifted and lowered by the lifting means such that the body part is lifted into its lifted position and lowered from its lifted position into its retracted position. The body part may further comprise a base part that can be covered by the cover part similar to a shoe box having a corpus and a lid. The base part can receive the drive unit and the lifting means, wherein the latter are configured for aforesaid lifting and lowering of the cover part. Such a two-part configuration is simple manufacture and facilitates maintenance.

The drive unit may comprise a belt drive. The belt drive can e.g. be driven by an electric motor and may comprise multiple belts that function as propulsion means. Such a belt drive is simple, cost saving, and highly efficient in use. Furthermore, a belt drive provides very high traction. For example, the belt drive comprises a gear that enables high torque to be applied to the propulsion belt(s).

Two or more of the devices as described above can be part of a system for moving cargo above a floor inside of an aircraft, wherein the system is arranged to synchronize a moving of the devices and lifting/lowering of the body parts of the devices. For this purpose, the system may comprise a control unit that may control the drive unit and/or the lifting means of the devices, e.g. to control the speed and position of the devices. For example, the drive units of the devices may be controlled such that they are moving by the same speed and/or to the same position. Also, the lifting means of the devices may be controlled such that the body parts of the devices are always in the same height. Further, the system may be arranged to enable a manual controlling of the devices via a cable. Alternatively, such control can be radio-controlled or automatically controlled.

In an example, an aircraft comprises a system as described above, wherein the aircraft comprises one guiding unit for each device, wherein the guiding is arranged to guide the device beneath the cargo. Such a guiding unit can be, e.g. a U-shaped indentation of an aircraft floor structure, as described above and enables that the devices can be moved under the cargo very fast and that existing indentations respectively profiles of a floor structure can be reused and changes to the aircraft structure are not necessary.

According to the method for moving cargo above a floor inside of an aircraft at least two devices as described above are provided in an aircraft. In an example, the devices are provided in an aircraft that comprises a floor, e.g. a cargo floor, with a U-shaped indentation in that the devices fit to be positioned under the cargo to be moved. The devices are positioned beneath the cargo, wherein the body parts of the devices are in their retracted positions and the positioning is done by the driving units of the devices. The body parts are lifted into their lifted positions by the lifting means of the devices such that the weight of the cargo is supported by the body parts and the cargo is lifted above the floor inside of the aircraft. Then, the cargo is moved to a desired position by moving each of the devices to a desired position. After that, the body parts are lowered into their retracted positions by the lifting means of the devices such that the cargo is lowered and the devices are moved away vertically from the cargo.

After that, each of the devices can be moved to another desired position and the aforementioned steps can be repeated once or several times to move more cargo to desired positions. In an example, the moving of the devices and the lifting of the body parts of the devices are synchronized, for example automatically synchronized, e.g. by a control unit as described above.

BRIEF DESCRIPTION OF THE DRAWINGS

The various embodiments will hereinafter be described in conjunction with the following drawing figures, wherein like numerals denote like elements, and:

FIG. 6 is a flowchart of the procedural steps according to an example of a method for moving cargo above a floor inside of an aircraft, and FIG. 7A-FIG. 7B show schematically four devices that move cargo above a cargo floor of an aircraft at different steps according to the method shown in FIG. 6.

FIG. 8A-FIG. 8B show schematically four devices that move cargo above a cargo floor of an aircraft at different steps according to the method shown in FIG. 6.

FIG. 9A-FIG. 9B show schematically four devices that move cargo above a cargo floor of an aircraft at different steps according to the method shown in FIG. 6.

FIG. 10A-FIG. 10B show schematically four devices that move cargo above a cargo floor of an aircraft at different steps according to the method shown in FIG. 6.

FIG. 11A-FIG. 11B show schematically four devices that move cargo above a cargo floor of an aircraft at different steps according to the method shown in FIG. 6.

FIG. 12A-FIG. 12B show schematically four devices that move cargo above a cargo floor of an aircraft at different steps according to the method shown in FIG. 6.

Basically, identical or similar components have the same reference characters. The illustrations in the figures are merely diagrammatic and not to scale.

DETAILED DESCRIPTION

The following detailed description is merely exemplary in nature and is not intended to limit the disclosed embodiments or the application and uses thereof. Furthermore, there is no intention to be bound by any theory presented in the preceding background detailed description.

Figure 1:
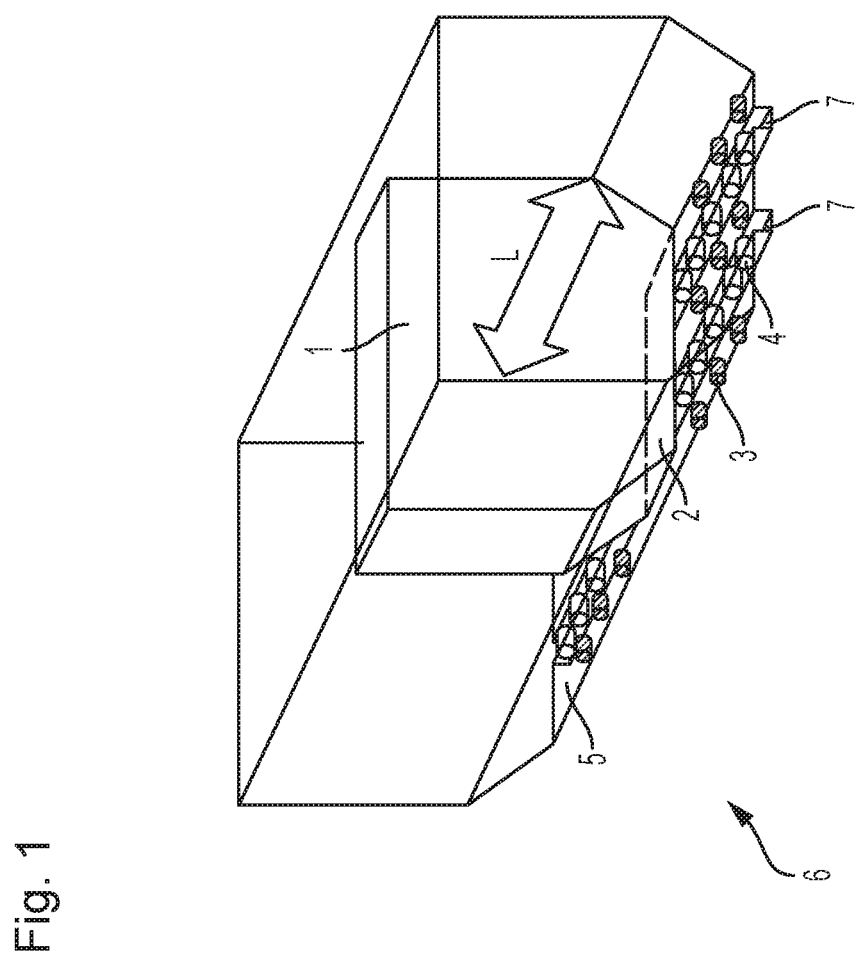
FIG. 1 shows a schematically perspective view of a known system for moving cargo above a floor inside of an aircraft.

FIG. 1 is a container 1 having a rigid under floor 2 that is represented with dashed lines. The container 1 stands with its rigid under floor 2 on permanently installed Power Drive Units (PDUs) 3 and also permanently installed free-wheeling rollers 4 that support the weight of the container 1. For reasons of clarity, only each one of the PDU's 3 and the rollers 4 are designated with a reference sign. The PDU's 3 and the rollers 4 are rotatably mounted in a cargo floor 5 that is part of an aircraft 6, wherein the aircraft 6 is only partially shown in FIG. 1. The cross section of the cargo floor 5 comprises two spaced apart U-shaped indentations 7 that are orientated in a longitudinal direction of the aircraft 6 as indicated by double arrow L. The rollers 4 are mounted in the indentations 7 and the PDU's in-between the indentations 7 such that both the PDU's 3 and the rollers 4 contact the rigid under floor 2 of the container 1. The PDU's 3 can be driven such that they rotate and move the container 1 in the longitudinal direction L of the aircraft 6.

Figure 2:
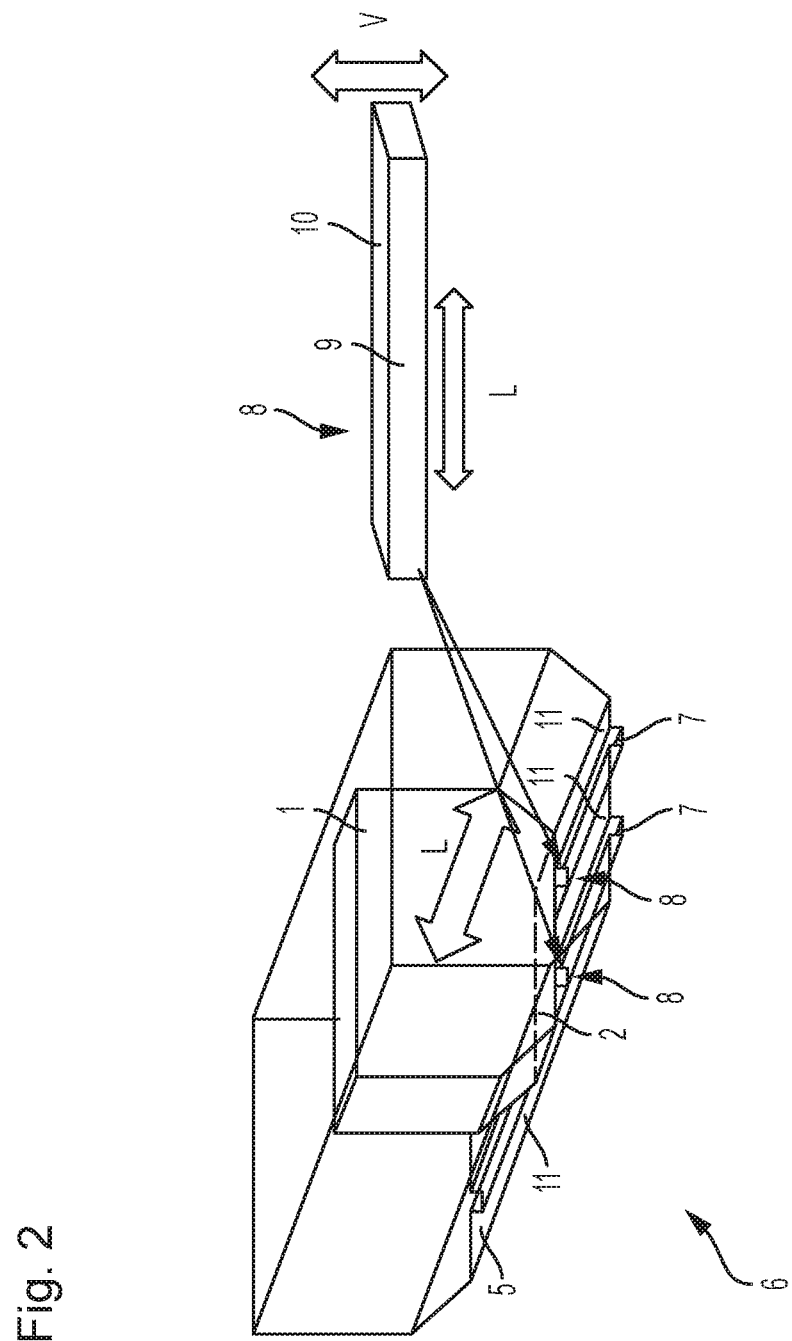
FIG. 2 shows a schematically perspective view of two exemplary devices for moving cargo above a floor inside of an aircraft.

With reference to FIG. 2 of the drawings, the same container 1 as shown in FIG. 1 is standing on two identical devices 8 for moving cargo having a rigid under-floor 2, in this case the container 1, above a floor, in this case a cargo floor 5, of an aircraft 6. Similar to FIG. 1 the aircraft 6 is also shown only partially in FIG. 2. The device 8 comprises a body part 9 having a cuboid shape. The body part 9 is dimensioned to fit in two U-shaped indentations 7 of the cargo floor 5. Also, the body part 9 is designed for supporting the weight of the container 1, wherein the rigid under-floor 2 of container 1 is supported by each one top surface 10 of the body parts 9. The body parts 9 can be lifted a few centimeters in a vertical direction as indicated by double arrow V by lifting means that are not shown in FIG. 2 (please see FIGS. 3 to 5). In this manner the body parts 9 are lifted into a lifted position. Also, the body parts 9 can be lowered in the vertical direction V by the lifting means from their lifted position into retracted positions in that they can be moved beneath the container 1. In their retracted positions, the top surfaces 10 of the body parts 9 run vertically stepped below straight sections 11 of the cargo floor 5, wherein the straight sections 11 are situated adjacent to the two U-shaped indentations 7.

If the body parts 9 are in their retracted positions, the rigid under floor 2 of the container 1 is supported by the straight sections 11 of the cargo floor 5, but not by the body parts 9 of the devices 8. In contrast, if the body parts 9 have been lifted in their lifted positions, the rigid under floor 2 of the container 1 is supported by the body parts 9 of the devices 8, but not by the straight sections 11 of the cargo floor 5. In their lifted positions, the top surfaces 10 of the body parts 9 run vertically stepped above the straight sections 11 of the cargo floor 5. As a result of lifting the body parts 9 from their retracted position into their lifted position, the container 1 is also lifted by the devices 8.

Figure 3:
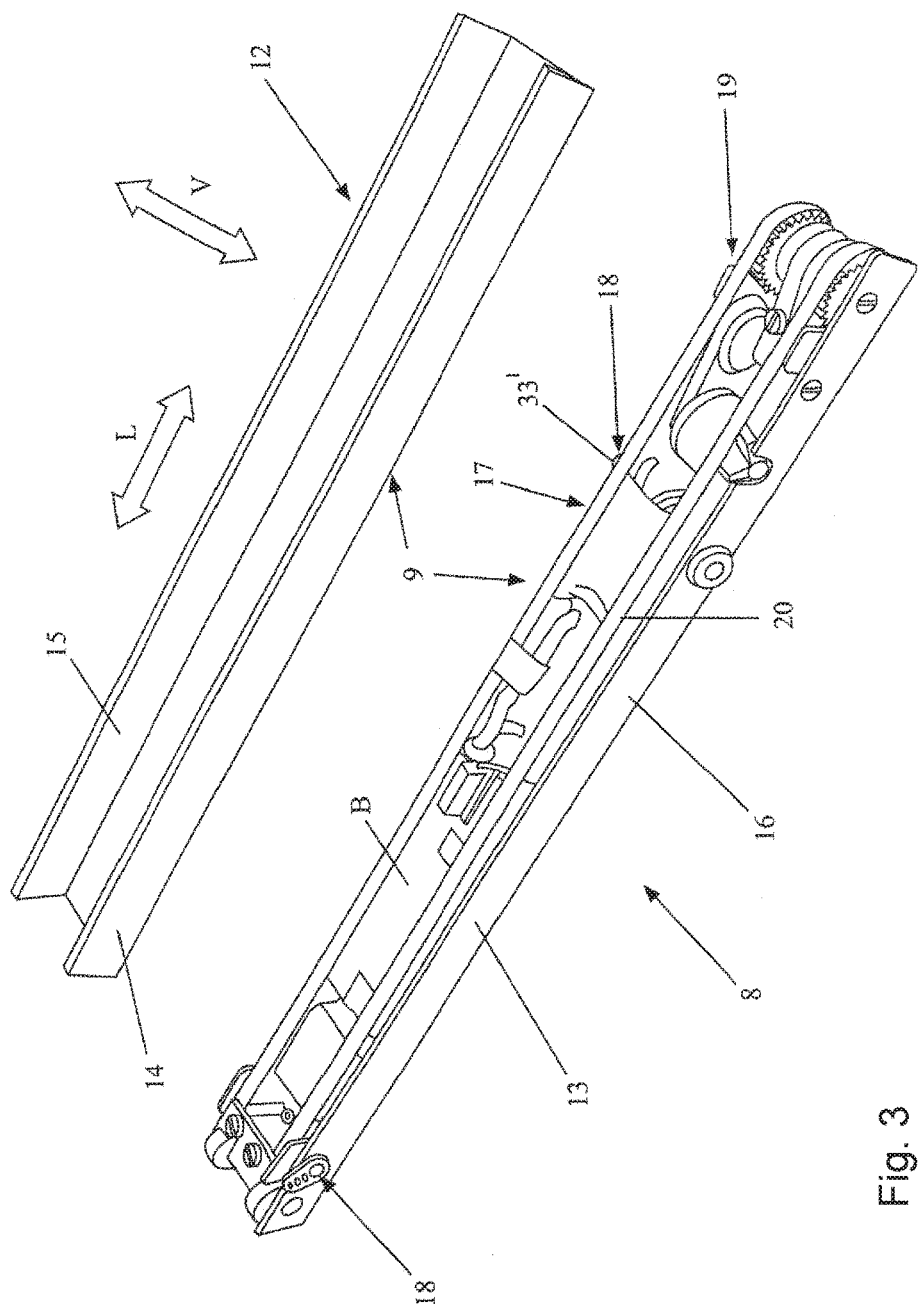
FIG. 3 shows a perspective view of one of the devices as per FIG. 2.
Figure 4:
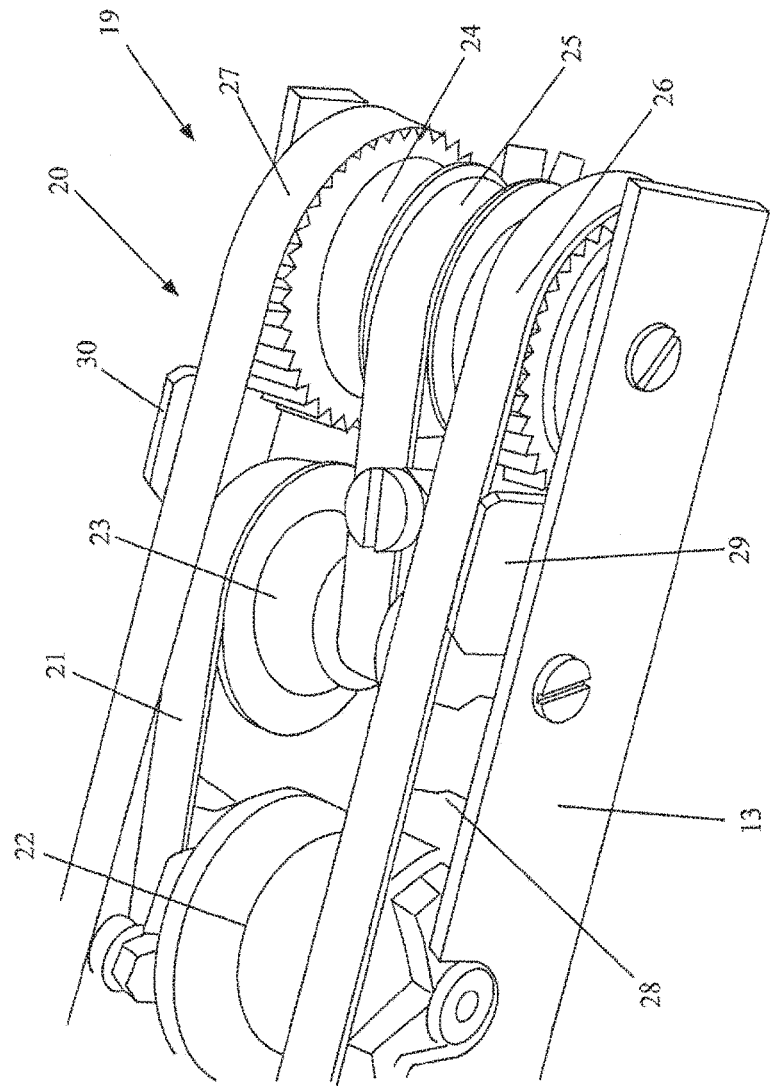
FIG. 4 shows an enlarged detailed view of the right end section of the base part shown in FIG. 3.
Figure 5:
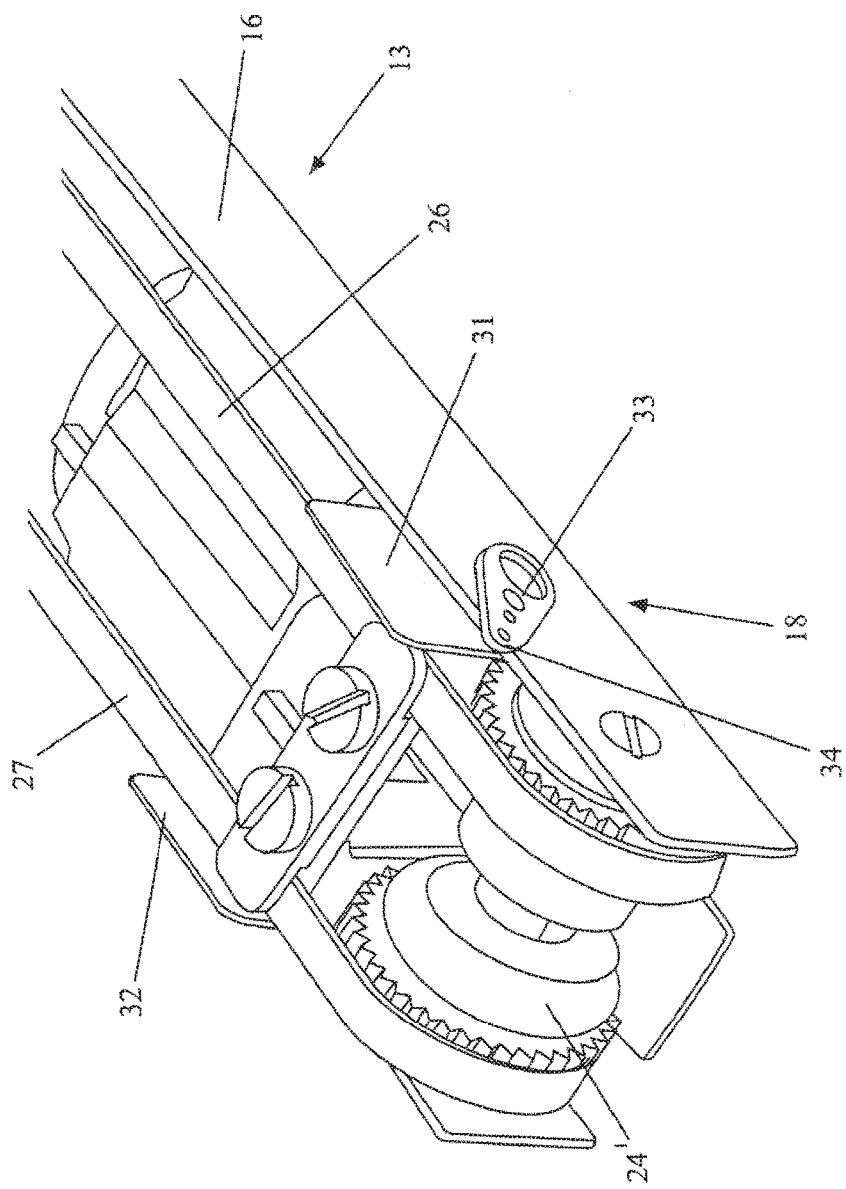
FIG. 5 shows an enlarged detailed view of the left end section of the base part shown in FIG. 3.

The devices 8 each comprise a drive unit that is not shown in FIG. 2 (please see FIGS. 3 to 5). The drive unit is arranged for moving the body part in its longitudinal direction that is in the shown example parallel to the longitudinal direction L of the aircraft. By such a moving in the longitudinal direction the, container 1, weight of which is completely supported by the devices 8, can be moved in the longitudinal direction L, if the devices 8 are in their lifted position. In other possible configurations of the devices 8, the drive unit can also be arranged to move the devices 8 respectively, their body parts 9, in another direction, e.g. in a lateral direction of the aircraft 6 that is perpendicular to the longitudinal axis L and the vertical axis V. Also, it is possible that the drive units are configured to move the devices 8 respectively the body parts 9 in many different directions, e.g. by comprising a suitable steering.

The two devices 8 shown in FIG. 2 are part of a system for moving cargo, in the shown example a container 1, above a floor, in the shown example a cargo floor 5, inside of an aircraft 6. The system is arranged to synchronize a moving of the devices 8, a lifting and a lowering of the body parts 9 of the devices 8.

FIGS. 3 to 5 show one of the devices 8 as per FIG. 2 in a more detailed way. As shown in FIG. 3, the device 8 is powered by a battery B and comprises a body part 9 with a U-shaped cover part 12 and an also substantially U-shaped base part 13. The base part 13 can be covered by the cover part 12 such that two parallel legs 14 and 15 of the U-shaped cover part 12 run parallel to two parallel legs 16 and 17 of the U-shaped base part 13. When covering the base part 13, the cover part 12 can be lifted and lowered in a vertical direction as indicated by double arrow V. This lifting and lowering is done by lifting means 18 in such a way that the body part 9 is lifted respectively extended into its lifted position and lowered respectively retracted from its lifted position into its retracted position. The base part 13 receives a drive unit 19 and the lifting means 18, wherein the drive unit 19 comprises a belt drive 20 and is configured for moving the body part 9 in a longitudinal direction L.

The right end section of the base part 13 with a part of the belt drive 20 is shown in an enlarged view by FIG. 4. The belt drive 20 comprises a first belt 21 that runs parallel to the longitudinal direction L on a drive shaft of an electric motor 22 and on a first roller 23 that is rotatably mounted in the base part 13 of the body part 9. A second roller 24 is also rotatably mounted in the base part 13 of the body part 9. A second belt 25 runs parallel to the first belt 21 on the first roller 23 and the second roller 24. A third belt 26 and a fourth 27 belt a run parallel to the second belt 25 on larger diameter sections of the second roller 24 and, in the same way, on a third roller 24' situated on the opposite left end of the base part 13 (please see FIGS. 3 and 5). The larger diameter sections of the second roller 24 are taller than the height of the legs 16 and 17 of the base part 13 that comprises a base plate 28 extending between the two legs 16 and 17 of the base part 13 and comprising apertures in the areas of the second roller 24 and the third roller 24'. Thus, the third belt 26 and the fourth belt 27 run below the base plate 28 outside of the base part 13, can contact a surface below the base part 13 and can move the body part 9 above such a surface, e.g. a cargo floor 5 of an aircraft 6, if the electric motor 22 drives the first belt 21. In this configuration the first roller 23, the second roller 24, the first belt 21 and the second belt 25 serve as a gear that distributes the power of the electric motor 22 to the third belt 26 and the fourth belt 27. The third belt 26 and the fourth belt 27 serve as means for crawling.

Further, each two guiding members 29 to 33 are fixed to the inner sides of the two legs 16 and 17 of the base part 13 in the area of its left and its right end section. The two legs 14 and 15 of the cover part 12 can be slid over the guiding members 29 such that the cover part 12 covers the base part 13 of the device 8. Further, the guiding members 29 to 33 also serve as distant members as they extend high enough in the vertical direction v that they keep the cover part 12 in clear distance to the third belt 26 and the fourth belt 27, if the cover part 12 covers the base part 13 in the way as described above.

The left end section of the base part 13 with a part of the belt drive 20 and the lifting means 18 is shown in an enlarged view by FIG. 5. The lifting means 18 comprise a cam 33 that is rotatably mounted in a leg 16 of the base part 13. Similarly, another cam 33' is rotatably mounted in the other leg 17 of the base part 13 (please see FIG. 3). The cams 33, 33' can be driven e.g. by an electric motor, suitable hydraulic or pneumatic means. The cams 33 and 33' can rotate and are long enough such that their free ends 34 can contact a top plate 35 of the cover part 12 and lift the cover part 12 a few centimeters in the vertical direction V, if the cover part 12 is covering the base part 13 in the way as described above.

FIG. 6 shows an example of a method for moving cargo above a floor inside of an aircraft. FIGS. 7 to 12 illustrate how the procedural steps of the method according to FIG. 6 are executed, wherein Figs. indicated with an "a", e.g. "FIG. 7A", show schematically top views and Figs. indicated with a "b", e.g. "FIG. 7B" show schematically side views.

In a first step 100 (FIGS. 7A and 7B), also referred to as step a), the body parts 9 of four devices 8 as per FIG. 3 are provided in U-shaped indentations 7 of a cargo floor 5 of an aircraft 6 that is only shown partially in FIGS. 7 to 12. Also, for the purpose of clarity only one of the four devices 8, their body parts 9 and one of the four indentations 7 are indicated with a reference sign. A cargo, in this case a container 1, having a rigid under-floor 2 is partly standing on a first ball mat 36 and a second ball mat 37, that are positioned in an entrance area 38 of the aircraft 6, wherein the second ball mat 37 is permanently installed in the aircraft 6. The ball mats 36 and 37 are configured for moving cargo like the container 1 omnidirectionally within the entrance area 38. Power Unit Drives (PDU's) 3 are provided in the second ball mat 37 and are configured for rotating about the longitudinal axis of the aircraft 6, as indicated by double arrow L, and for moving cargo in a lateral direction of the aircraft 6, as indicated by double arrow Lat. For the purpose of clarity only one of the PDU's 3 is indicated with a reference sign. In their shown positions, the devices 8 are positioned parallel to each other and still apart from the container in the U-shaped indentations 7. The devices 8 are radio controlled or cable controlled and their body parts 9 are retracted in their retracted positions in that their top surfaces 10 run vertically stepped below straight sections 11 of the cargo floor 5, wherein the straight sections 11 are situated adjacent to the four U-shaped indentations 7. All devices 8 are synchronized, that especially means that their drive units and lifting means (not shown in FIGS. 7 to 12, please see FIGS. 3 to 5) are coordinated such that the devices 8 are moving at the same speed to same positions in the longitudinal direction L of the aircraft 6 and that the body parts 9 of the devices 8 are lifted and lowered in the same extend in a vertical direction of the aircraft 6 as indicated by double arrow V.

In a second step 200 (FIGS. 8A and 8B), also referred to as step b), the devices 8 are positioned beneath the container 1 that now fully stands on the second ball mat 37 and wherein the body parts 9 of the devices 8 are still in their retracted positions.

In a third step 300 (FIGS. 9A and 9B), also referred to as step c), the body parts 9 of the devices 8 are lifted into their lifted positions by the lifting means of the devices 8 such that the weight of the container 1 is supported by the body parts 9 of the devices 8 and the container 1 is lifted above the floor 5 inside of the aircraft 6.

In a fourth step 400 (FIGS. 10A and 10B), also referred to as step d), the container 1 is moved to a desired position P by moving the four devices 8 to the desired position P, wherein the desired position P of the four devices 8 can deviate slightly from the desired position P of the container 1.

In a fifth step 500 (FIGS. 11A and 11B), also referred to as step e), the body parts 9 of the devices 8 are lowered into their retracted positions by the lifting means of the devices 8 such that the container 1 is also lowered and the body parts 9 of the devices 8 are moved away vertically v from the container 1.

In a sixth step 600 (FIGS. 12A and 12B), also referred to as step f), the body parts 9 of the devices 8 are still in their retracted positions and the devices 8 are moved to another desired position P' beneath another container 1' that shall be moved to a third desired position P''' next to the first desired position P as described above.

While at least one exemplary embodiment of the present invention(s) is disclosed herein, it should be understood that modifications, substitutions and alternatives may be apparent to one of ordinary skill in the art and can be made without departing from the scope of this disclosure. This disclosure is intended to cover any adaptations or variations of the exemplary embodiment(s). In addition, in this disclosure, the terms "comprise" or "comprising" do not exclude other elements or steps, the terms "a" or "one" do not exclude a plural number, and the term "or" means either or both. Furthermore, characteristics or steps which have been described may also be used in combination with other characteristics or steps and in any order unless the disclosure or context suggests otherwise. This disclosure hereby incorporates by reference the complete disclosure of any patent or application from which it claims benefit or priority.

What is claimed is:

1. A device for moving cargo along a floor inside an aircraft, comprising:
   a body part designed for supporting the weight of the cargo,
   lifting means arranged for lifting the body part into a lifted position and for lowering the body part from the lifted position into a retracted position, and
   a drive unit arranged for moving the body part,
   wherein the drive unit comprises a belt drive, and
   wherein said belt drive comprises a gear and at least one belt that contacts a surface of the floor inside the aircraft to move the body part above the surface.

2. The device as claimed in claim 1, wherein the drive unit is arranged for moving the body part in two directions perpendicular to each other.

3. The device as claimed in claim 1, wherein the body part comprises a cuboid shape and is dimensioned to fit in a U-shaped indentation of an aircraft floor structure.

4. The device as claimed in claim 1, wherein the body part comprises a cover part which is lifted and lowered by the lifting means such that the body part is lifted to the lifted position and lowered from the lifted position into the retracted position.

5. An aircraft, comprising:
   a floor inside of the aircraft; and
   a system for moving cargo above the floor, the system comprising:
      a plurality of devices configured to move cargo along the floor, each of the devices comprising:
         a body part designed for supporting the weight of the cargo;
         lifting means arranged for lifting the body part into a lifted position and for lowering the body part from the lifted position into a retracted position; and
         a drive unit arranged for moving the body part, wherein the drive unit comprises a belt drive, and wherein said belt drive comprises a gear and at least one belt; and
      one guiding unit for each device, wherein the guiding unit is arranged to guide the device beneath the cargo, wherein the at least one belt contacts a surface of the guiding unit to move the body part above the surface;
   wherein the system is arranged to synchronize moving of the devices and lifting of the body parts of the devices.

* * * * *